(12) United States Patent
Hübsch et al.

(10) Patent No.: US 6,462,205 B1
(45) Date of Patent: Oct. 8, 2002

(54) METHOD OF PREPARING BENZOFURANDIONE OXIME DERIVATIVES

(75) Inventors: Walter Hübsch, Wuppertal (DE); Lubbertus Mulder, Hagen (DE); Bernd Gallenkamp, Wuppertal (DE); Herbert Gayer, Monheim (DE); Reinhard Lantzsch, Wuppertal (DE)

(73) Assignee: Bayer Aktiengesellscahft, Leverkusen (DE)

( * ) Notice: Subject to any disclaimer, the term of this patent is extended or adjusted under 35 U.S.C. 154(b) by 0 days.

(21) Appl. No.: 09/937,420

(22) PCT Filed: Sep. 26, 2001

(86) PCT No.: PCT/EP00/02283

§ 371 (c)(1),
(2), (4) Date: Sep. 6, 2001

(87) PCT Pub. No.: WO00/58299

PCT Pub. Date: Oct. 5, 2000

(30) Foreign Application Priority Data

Mar. 27, 1999 (DE) .......................... 199 14 142

(51) Int. Cl.⁷ .......................... C07D 307/00
(52) U.S. Cl. .......................... 549/303
(58) Field of Search ................ 549/303, 467

(56) References Cited

U.S. PATENT DOCUMENTS 6,005,104 A   12/1999  Gallenkamp et al. ......... 544/65
6,093,837 A   7/2000   Gallenkamp et al. ........ 549/467
6,150,521 A   11/2000  Gayer et al. .................. 544/65

FOREIGN PATENT DOCUMENTS

| EP | 0 846 691 | 6/1998 |
| WO | 93/07116 | 4/1993 |
| WO | 95/04728 | 2/1995 |
| WO | 95/24396 | 9/1995 |

OTHER PUBLICATIONS

Synthetic Communications, 23(16), 1993, pp. 2279–2284, Franco Ghelfi, Romano Grandi and Ugo M Pagnoni, Carbonyl Regeneration From Oximes and Semicarbazones by Trimethylchlorosilane–Dimethylsuphoxide.

Venkateswara Rao K. et al:, "Reactivity of 2–Hydroxy–Omega–Nitroacetophenones: Synthesis of 2–Oximinocoumaranones", Proceedings of the Indian Academy of Sciences. Section A Physical Sciences, IN, Bagalore, Bd. 83A, Nr. 6, 1976, Seiten 238–242, XP002059228.

Loth H. et al:, "Eine Neue Synthese Von 2–Acyloxyimino–Cumaranonen", Archiv der Pharmazie, DE, VCH Verlagsgesellschaft MBH, Weinheim, Bd. 306, Nr. 2, Feb. 1, 1973, Seiten 122–126, XP002039748.

*Primary Examiner*—Amelia Owens
(74) *Attorney, Agent, or Firm*—Joseph C. Gil; Raymond J. Harmuth

(57) ABSTRACT

The present invention relates to a novel process for preparing benzofurandioneoxime derivatives by reacting benzofurandioneoxime derivatives with acids.

19 Claims, No Drawings

METHOD OF PREPARING BENZOFURANDIONE OXIME DERIVATIVES

The present invention relates to a novel process for preparing benzofurandioneoxime derivatives.

A process for preparing benzofurandione methyl oximes has already been described (cf. WO 95/24396). A process for preparing carbonyl compounds from oximes has been described by Grandi et al. (cf. R. Grandi et al., Synthetic Communications, 23 (16), 2279 (1993)).

However, the compounds prepared by these processes are only obtainable in moderate yields. These processes furthermore have the disadvantage that the product is obtained as a E/Z isomer mixture.

It has now been found that compounds of the formula (I)

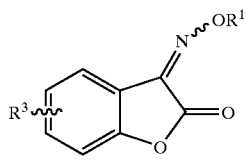

in which
$R^1$ represents substituted or unsubstituted alkyl,
$R^3$ represents hydrogen, substituted or unsubstituted alkyl, alkoxy, halogenoalkoxy or halogen,
are obtained when compounds of the formula (II)

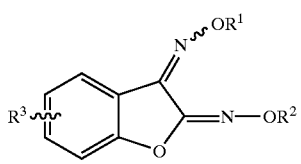

in which
$R^1$ and $R^3$ are each as defined above and
$R^2$ represents hydrogen, or substituted or unsubstituted alkyl, are reacted with acids, or with trialkylsilyl chloride in the presence of dialkyl sulphoxide, if appropriate in a diluent and/or a solvent.

Preference is given to processes in which compounds of the formula (II) are reacted with acids.

In the reaction with a trialkylsilyl chloride in the presence of dialkyl sulphoxide, preference is given to using trimethylsilyl chloride in the presence of dimethyl sulphoxide.

For the purposes of the invention, acids are relatively highly concentrated acids, in particular mineral acids.

Preferred mineral acids are sulphuric acid, preferably 10 to 90% strength sulphuric acid, in particular half-concentrated commercial sulphuric acid, and/or phosphoric acid, preferably 20 to 95% strength phosphoric acid, in particular commercial 85% strength phosphoric acid.

Diluents and/or solvents used, by way of example and by way of preference, in the reaction of compounds of the formula (II) with acids are water; alcohols, in particular methanol; ethers, in particular dimethoxyethane, tetrahydrofuraii, methyl tert-butyl ether or tert-amyl methyl ether; alkylnitriles, in particular acetonitrile; ketones, in particular acetone, or solvent mixtures thereof, in particular alcohol/water mixtures.

When reacting compounds of the formula (II) with trialkylsilyl chloride in the presence of dialkyl sulphoxide, the diluents and/or solvents used are ethers, in particular dimethoxyethane, tetrahydrofuran, methyl tert-butyl ether or tert-amyl methyl ether; alkylnitriles, in particular acetonitrile; N-methyl-pyrrolidone; alkanecarboxylic esters, in particular acetic ester; ketones, in particular acetone, or solvent mixtures thereof.

The reaction of compounds of the formula (II) with acids is carried out in a temperature range of from 0° C. to 100° C., preferably in a temperature range of from 20° C. to 80° C.

The reaction of compounds of the fomiula (II) with trialkylsilyl chloride in the presence of dialkyl sulphoxide is carried out in a temperature range of from 0° C. to the reflux temperature of the mixture in question, preferably at reflux temperature.

The reaction of compounds of the formula (II) is carried out at atmospheric pressure, at elevated or at reduced pressure, preferably at atmospheric pressure.

The compounds of the formula (II) are employed as E/Z isomer mixtures or as pure isomers.

The compounds of the formula (I) obtainable by the process according to the invention are then obtained in the form of the isomer mixtures or in the form of pure isomers. The isomer mixtures obtained can, if appropriate, be separated into the pure isomers by customary methods, for example by chromatograipiy.

The starting materials are defined by formula (II) above.

In the definitions, $R^1$, $R^2$ and $R^3$ of the formula (II) are saturated or unsaturated hydrocarbon chains, such as alkyl, alkoxy or halogenoalkoxy, in each case straightchain or branched. Alkyl in particular represents $C_1$–$C_4$-alkyl, in particular methyl, ethyl, n-propyl, i-propyl, n-butyl, s-butyl, t-butyl or i-butyl. Alkoxy in particular represents $C_1$–$C_4$-alkyl, in particular methoxy, ethoxy, n-propoxy, i-propoxy, n-butoxy, s-butoxy, t-butoxy or i-butoxy.

Preferred substituents for alkyl in the meaning of $R^2$ are hydroxyl, alkoxy, alkyloxycarbonyl or halogen.

Here, halogen generally represents fluorine, chlorine, bromine or iodine, preferably fluorine, chlorine or bromine, in particular fluorine or chlorine.

In the formula (II), $R^1$ preferably represents methyl.

In the formula (II), $R^2$ preferably represents hydrogen or 2-hydroxy-ethyl, in particular hydrogen.

In the formula (II), $R^3$ preferably represents hydrogen. FSome of the starting materials of the formula (II) are known. The compounds 2-hydroximino-3-methoximino-2,3-dihydro-benzofuran and 2-(2-hydroxyethoxyimino)-3-methoxiniino-2,3-dihydro-benzofuran used as starting materials are described in DE-A-19706399, DE-A-19706396 and EP-A-0 846 691. The compounds of the formula (II) which are not yet known can be prepared by the processes described in DE-A-19706399, DE-A-19706396 and/or EP-A-0 846 691.

All other starting materials are customary conmmercial products, or they can be prepared from these by simple processes.

Particular preference is given to processes in which compounds of the formula (II) are reacted with half-concentrated commniercial sulphuric acid and/or comnmercial half-concentrated 85% strength phosphoric acid, at temperatures of from 20° C. to 80° C.

A decisive advantage of the process according to the invention is the yield, which is increased compared with the known processes. A further advantage of the process according to the invention consists in the fact that, when isomer mixtures are used, the E isomers are formed predominantly. Moreover, it is very surprising for the person skilled in the art that the reaction of compounds of the formula (II) can be carried out in acidic medium.

The process is used for preparing important intermediates of the formula (I) which facilitates the production of known pesticides.

The examples below serve to illustrate the invention. However, the invention is not limited to the examples.

Preparation Examples for 3-Methoximino-2-oxo-2, 3-dihydrobenzofuran (1)

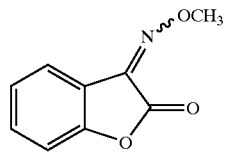

(1)

EXAMPLE 1

1.9 g (0.1 mol) of 2-hydroximino-(E)-3-methoximino-2, 3-dihydro-benzofuran are stirred at room temperature in 10 ml of half-concentrated commercial sulphuric acid for 18 hours. The mixture is subsequently admixed with 300 ml of water and extracted three times with 100 ml of dichloromethane each time, and the combined organic phases are washed with in each case 100 ml of 1N NaOH and water, dried over $Na_2SO_4$ and concentrated to dryness.

Yield: 1.7 g (93% of theory);

NMR ($CDCl_3$): 4.34 ppm (s, 3H), 7.15 ppm (d, 1H), 7.22 ppm (t, 1H), 7.50 ppm (t, 1H), 7.97 ppm (dd, 1H).

EXAMPLE 2

4.7 g (0.02 mol) of 2-(2-hydroxy-ethoximino)-3-methoximino-2,3-dihydrobenzofuran E/Z mixture (55.6% of E isomer, 43.5% of Z isomer) are stirred at 55° C. in 20 ml of 85% strength phosphoric acid for two hours. Work-up and isolation are carried out analogously to Example 1.

Yield: 3.4 g of a liglht-beige solid (90.9% E, 4.6% Z;=96% of theory);

EXAMPLE 3

4.42 kg (23.0 mol) of 2-hydroximino-3-methoximino-2, 3-dihydro-benzofuran are stirred at 55° C. in 28 l of 85% strength o-phosphoric acid for three hours. The mixture is cooled to room temperature, and 12 l of ice-water are added dropwise with cooling. This suspension is stirred into 100 l of ice-water and filtered off with suction after 20 min, and the filter cake is washed with 40 l of water until the filtrate reacts neutral. The residue is stirred in 70 l of saturated $NaHCO_3$ solution and filtered off with suction, and the filter cake is washed with 25 l of water and dried at 50° C.

Yield: 3161 g (=77.6% of theory) of a light-beige solid

EXAMPLE 4

1.9 g (0.1 mol) of 2-hydroximino-(E)-3-methoximino-2, 3-dihydro-benzofuran are stirred at 55° C. in 10 ml of 85% strength phosphoric acid for two hours. The mixture is allowed to cool to room temperature, admixed with 300 ml of water and extracted three times with 100 ml of dichloromethane each time, and the combined organic phases are washed with in each case 100 ml of 1N NaOH and water, dried over $Na_2SO_4$ and concentrated to dryness.

Yield: 1.8 g of a light-beige solid, content by HPLC: 98.1% of E isomer (=100% of theory)

EXAMPLE 5

Analogously to Example 4, 2.3 g (0.12 mol) of 2-hydroximino-3-methoximino-2,3-dihydro-benzofuran E/Z mixture (68.5% of E, 31.2% of Z) are reacted at 70° C. in 12 ml of 85% strength phosphoric acid for two hours. Work-up is carried out analogously to Example 4.

Yield: 1.9 g of E/Z mixture (88.2% of E, 7% of Z) (=85% of theory); log p 2.20 (E isomer); log p 2.14 (Z isomer).

EXAMPLE 6

500 g of sea sand are added to 768.7 g (4.0 mol) of 2-hydroximino-3-methoximino-2,3-dihydro-benzofuran in 3.0 l of acetonitrile, and the mixture is heated to 55° C. 877.2 g (12.0 mol) of dimethyl sulphoxide and 1303.7 g (12.0 mol) of trimethylchlorosilane are then simultaneously added dropwise over a period of 30 minutes. The reaction mixture is stirred at 55° C. for one hour and under reflux for one hour, until evolution of gas has ceased. The mixture is subsequently cooled to 20° C., the suspension is filtered off with suction and the filter cake is washed with acetonitrile. The orange filtrate is added dropwise over a period of 30 minutes to 18 l of ice-water and 2 l of petroleum ether. The suspension is stirred at 20° C. for 30 minutes, the product depositing in the upper petroleum ether phase. The lower aqueous phase is drawn off and the product in. the PE phase is filtered off with suction and washed with 1.5 l of petroleum ether, 4.0 l of water and 1.0 l of petroleum ether and dried at 40° C. under reduced pressure.

Yield: 584 g=82.4% of a light-pink solid.

What is claimed is:

1. A process for preparing a compound of the formula (I),

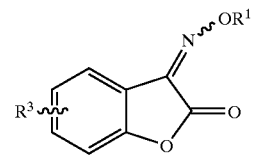

(I)

in which
R[1] represents substituted or unsubstituted alkyl,
R[3] represents hydrogen, substituted or unsubstituted alkyl, alkoxy, halogenoalkoxy or halogen,
comprising the step of reacting:
a compound of the formula (II)

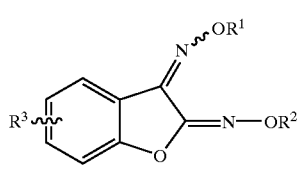

(II)

in which
R[1] and R[3] are each as defined above and
R[2] represents hydrogen, or substituted or unsubstituted alkyl, with
a compound selected from the group consisting of an acid and a trialkylsilyl chloride, said trialkylsilyl chloride being present in the presence of a dialkyl sulphoxide,
said process further optionally comprising the step of reacting said compound of the formula (I) with said compound selected from the group consisting of said acid and said trialkylsilyl chloride in a member selected from the group consisting of a diluent, a solvent, and combinations thereof.

2. The process according to claim 1, wherein said compounds of the formula (II) are reacted with one or more mineral acids.

3. The process according to claim 2, wherein said mineral acid is selected from the group consisting of sulphuric acid, phosphoric acid, and combinations thereof.

4. The process according to claim 3, wherein said mineral acid is selected from the group consisting of 10 to 90% strength sulphuric acid and 20 to 95% strength phosphoric acid.

5. The process according to claim 4, wherein the mineral acid is selected from the group consisting of half-concentrated commercial sulphuric acid and commercial 85% strength phosphoric acid.

6. The process according to claims 1, wherein said diluents and/or said solvents are selected from the group consisting of water, alcohols, ethers, alkylnitriles, ketones and combinations thereof.

7. The process according to claim 6, wherein said diluent and/or said solvent is selected from the group consisting of water, methanol, dimethoxyethane, tetrahydrofuran, methyl tert-butyl ether, tert-amyl methyl ether, acetonitrile, acetone or combinations thereof.

8. The process according to claim 1 wherein said diluent and/or said solvent used is water and/or methanol.

9. The process according to claim 1 or 8 wherein said dialkyl sulphoxide is dimethyl sulphoxide.

10. The process of claim 1 wherein the reaction of said acid with said compound of the formula (II) is carried out in a temperature range of from 0° C. to 100° C.

11. The process of claim 10 wherein the reaction is carried out in a temperature range of 20° C. to 80° C.

12. The process of claim 1 wherein the reaction of said trialkylsilyl chloride in the presence of said dialkyl sulphoxide with said compound of the formula (II) is carried out in a temperature range of from 0° C. to a reflux temperature of said reactants.

13. The process of claim 12 wherein said temperature is at said reflux temperature.

14. The process of claim 1 wherein said compounds of the formula (II) are employed as isomers selected from the group consisting of E/Z isomer mixtures and pure isomers.

15. The process of claim 1 wherein the compound of the formula (I) obtained by said process is obtained in a form selected from the group consisting of isomer mixtures and pure isomers.

16. The process of claim 1 wherein $R^1$, $R^2$, and $R^3$ of the formula (II) are $C_1$–$C_4$ alkyl.

17. The process of claim 16 wherein $R^1$, $R^2$, and $R^3$ of the formula (II) are selected from the group consisting of methyl, ethyl, n-propyl, i-propyl, n-butyl, s-butyl, t-butyl or i-butyl.

18. The process of claim 1 wherein $R^1$, $R^2$, and $R^3$ of the formula (II) are $C_1$–$C_4$ alkoxy.

19. The process of claim 1 wherein isomer mixtures of the formula (II) are employed whereupon E isomers of formula (I) are predominantly formed by said process.

* * * * *